(12) United States Patent
Darnell et al.

(10) Patent No.: US 8,915,880 B2
(45) Date of Patent: Dec. 23, 2014

(54) FUNNEL FOR A BREAST PUMP

(75) Inventors: Ian Philip Darnell, Eindhoven (NL); Graham Trevor Cook, Eindhoven (NL); Mark Robert Gabriel Douglas, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 13/821,251

(22) PCT Filed: Oct. 4, 2011

(86) PCT No.: PCT/IB2011/054346
§ 371 (c)(1),
(2), (4) Date: Mar. 7, 2013

(87) PCT Pub. No.: WO2012/049583
PCT Pub. Date: Apr. 19, 2012

(65) Prior Publication Data
US 2013/0190686 A1 Jul. 25, 2013

(30) Foreign Application Priority Data

Oct. 15, 2010 (EP) .................................. 10187709

(51) Int. Cl.
*A61M 1/06* (2006.01)
(52) U.S. Cl.
CPC ....................................... *A61M 1/06* (2013.01)
USPC ........................................................... 604/74
(58) Field of Classification Search
CPC ............ A61M 1/06; A61M 2001/064; A61M 2001/066; A61M 2001/0068; A61M 2205/073; A61M 2205/075; A61M 2001/0072; A61M 2205/076; A61M 2001/068; A61D 1/02; A61J 1/20; A61J 13/00; A61J 15/00
USPC ............................................... 604/74–76, 346
See application file for complete search history.

(56) References Cited

U.S. PATENT DOCUMENTS

| 3,911,920 | A | | 10/1975 | Susinn |
| 4,813,932 | A | * | 3/1989 | Hobbs ............................. 604/74 |
| 5,749,850 | A | * | 5/1998 | Williams et al. ................ 604/74 |
| 6,110,140 | A | * | 8/2000 | Silver .............................. 604/74 |
| 6,749,582 | B2 | * | 6/2004 | Britto et al. ..................... 604/74 |
| 7,413,557 | B2 | * | 8/2008 | Samson et al. .................. 604/74 |
| 2006/0116632 | A1 | | 6/2006 | Gillan |
| 2008/0255503 | A1 | | 10/2008 | Quackenbush et al. |

FOREIGN PATENT DOCUMENTS

| DE | 353958 C | 5/1922 |
| DE | 535390 C | 10/1931 |

* cited by examiner

*Primary Examiner* — Manuel Mendez

(57) ABSTRACT

The present invention relates to a funnel for a breast pump. Milk expressed from a user's nipple is known to pool at a user's breast. The funnel for a breast pump according to the present invention comprises a breast receiving portion (29) and a nipple receiving chamber (34) to receive a user's nipple. The nipple receiving chamber (34) is defined by an inner surface (36) of an outer wall (37), wherein the inner surface (36) of the outer wall (37) extends from the breast receiving portion (29), and a lower section (40) of the inner surface (36) diverges away from an opposing upper section (39) of the inner surface (36) and a user's nipple received in the nipple receiving chamber. The present invention also relates to a breast pump comprising a funnel.

14 Claims, 4 Drawing Sheets

FUNNEL FOR A BREAST PUMP

FIELD OF THE INVENTION

The present invention relates to a breast pump comprising a funnel having a breast receiving portion and a nipple receiving chamber to receive a user's nipple, a fluid passageway extending from the nipple receiving chamber along which milk expressed from a user's nipple is able to flow, and a vacuum pump unit chamber for receiving a vacuum pump unit to generate a vacuum in the nipple receiving chamber, the nipple receiving chamber being defined by an inner surface of an outer wall, wherein the inner surface of the outer wall extends from the breast receiving portion, and a lower section of the inner surface diverges away from an opposing upper section of the inner surface. Such a breast pump is operable to extract milk from a breast of a user.

BACKGROUND OF THE INVENTION

Breast pumps are well known devices for extracting milk from a breast of a user. A breast pump may be used if the baby or infant is not itself able to express milk from the breast, or if the mother is separated from the baby or infant, for example, if away from the baby at work. The use of a breast pump to express milk may also be used to stimulate and increase milk production in women with a low milk supply.

Breast pumps make use of a vacuum to induce milk expression from a nursing mother's breast. The pumping action of the device draws the milk from the nipple to a collection vessel, and the pressure and/or frequency may generally be adjusted to the preferences of the mother.

A known breast pump for extracting milk from a user's breast is shown in FIG. 1. Such a breast pump 1 comprises a main body 2 and a collection vessel 3, such as a feeding bottle or bag. The collection vessel 3 is attached to the main body 2 by a screw fitting.

A breast-receiving funnel 4 extends from the main body 2 for receiving the breast of a user. The funnel 4 has an inner surface 5 and comprises a breast receiving portion 6 and a throat 7. The breast receiving portion 6 is open at an outer end and the inner surface 5 of the funnel 4 converges from the outer end towards the throat 7 to form a hollow recess in which a breast is received.

The throat 7 is a generally cylindrical tube which extends from the breast receiving portion 6 to the main body 2. When a breast of a user (not shown) is received in the breast receiving portion 6 of the funnel, the nipple of a user is received in a nipple receiving space 8 defined by the throat 7 of the funnel 4.

A fluid path is defined by the breast receiving portion 6 and throat 7 of the funnel 4, through the main body 2, to the collection vessel 3 so that milk induced from a user's breast flows along the throat of the funnel 4, through the main body 2 to the collection vessel 3.

A vacuum pump unit 9 is formed in the main body 2 and generally comprises a resilient diaphragm 10 which is deformable in a vacuum chamber formed in the main body 2 along the fluid path to create a vacuum in the vacuum chamber, and therefore along the fluid path, by means of a user manually operating a handle 11 which acts on the diaphragm 10, or by means of an electric motor (not shown). A one way valve 12 is disposed along the fluid path between the vacuum chamber and the collection vessel 3 to prevent a vacuum being created in the collection vessel 3, but to allow milk to flow along the fluid path into the collection vessel 3.

However, a problem with known funnels for a breast pump and breast pump arrangements is that they need to be used with the user sat in an upright position or with the user leaning forwards, as shown in FIG. 1, to maximize the volume of expressed milk in the funnel that flows through to the collection vessel 3. Generally, if a user does not lean forward then the milk flows back towards the breast due to the inner surface 5 of the throat 7 of the funnel 4 forming an opposing incline, as shown in FIG. 2. This leads to milk pooling at the breast, leakage from the breast receiving portion 6 of the funnel 4 around the user's breast and ultimately loss of milk.

Expressed milk is considered to be very precious and is known to have a high emotional value to mothers that have expressed milk from their breasts. Therefore, this residual milk is considered to be a loss to a user, and this loss of milk may have an emotional impact on the user.

Furthermore, leaning forward for the full expression duration of 15 to 30 minutes is uncomfortable and prevents a user from relaxing. In order for milk to be produced in the milk glands to be released into the milk ducts a 'let-down' reflex has to occur. However, it is known that the time to 'let down reflex' will increase and milk production will be inefficient if the mother is uncomfortable and not relaxed.

A breast pump system is known from US 2006/0116632 A1 which attempts to deal with the above problems and allow a user to recline whilst using a breast pump by use of an insert for the breast pump and a strap arrangement. However, a problem with the breast pump system in this document is that the breast pump in which the insert is disposed must be maintained in an upright position to prevent pooling, even when a user is in a reclined position. Therefore, the angle that the user can lean back is limited before the breast pump abuts against the user's midriff.

A further disadvantage of the breast pump system recited in the above document is that the user's nipple extending into the insert of the breast pump system will contact and abut against the insert, which may cause abrasion or rubbing of the user's nipple and cause discomfort and/or soreness. Furthermore, two breast pumps must be used simultaneously in order for the breast pump system to operate successfully.

SUMMARY OF THE INVENTION

Therefore, it is an object of the invention to provide a funnel for a breast pump which substantially alleviates or overcomes the problems mentioned above.

A breast pump according to the present invention is characterised in that the vacuum pump unit chamber is formed in the fluid passageway.

Preferably, the breast receiving portion has a longitudinal axis and the lower section of the inner surface diverges away from the longitudinal axis of the breast receiving portion.

Conveniently, the upper section of the inner surface extends parallel to the longitudinal axis of the breast receiving portion.

The outer wall may further comprise an end surface extending from the upper section of the inner surface.

The breast pump may further comprise a fluid passageway extending from the nipple receiving chamber.

Conveniently, the fluid passageway extends from the lower section of the inner surface.

Advantageously, the fluid passageway extends parallel to the lower section of the inner surface.

Preferably, the fluid passageway is formed in the end surface of the nipple receiving chamber.

In one embodiment, the breast pump further comprises a fluid outlet extending from the fluid passageway which communicates between the fluid passageway and a milk collection vessel for receiving milk expressed from a user's nipple, wherein the fluid outlet extends downwardly from the fluid passageway so that milk falls towards the milk collection vessel.

A bottom section of a side wall of the fluid passageway may extend from the lower section of the inner surface to the fluid outlet.

Advantageously, a valve is disposed at a lower end of the fluid outlet (46) spaced from the bottom section of the side wall of the fluid passageway.

Conveniently, the vacuum pump unit comprises a deformable diaphragm with an actuating element extending therefrom to deform the diaphragm when the vacuum pump unit is actuated, the deformable diaphragm being disposed in the vacuum pump unit chamber formed in the fluid passageway, a longitudinal axis of the actuating element extending perpendicular to the fluid passageway.

Preferably, the nipple diaphragm chamber is disposed between the nipple receiving chamber and the fluid outlet.

BRIEF DESCRIPTION OF THE DRAWINGS

Preferred embodiments of the invention will now be described, by way of example only, with reference to the accompanying drawings, in which.

DETAILED DESCRIPTION OF THE EMBODIMENTS

Figure 3:
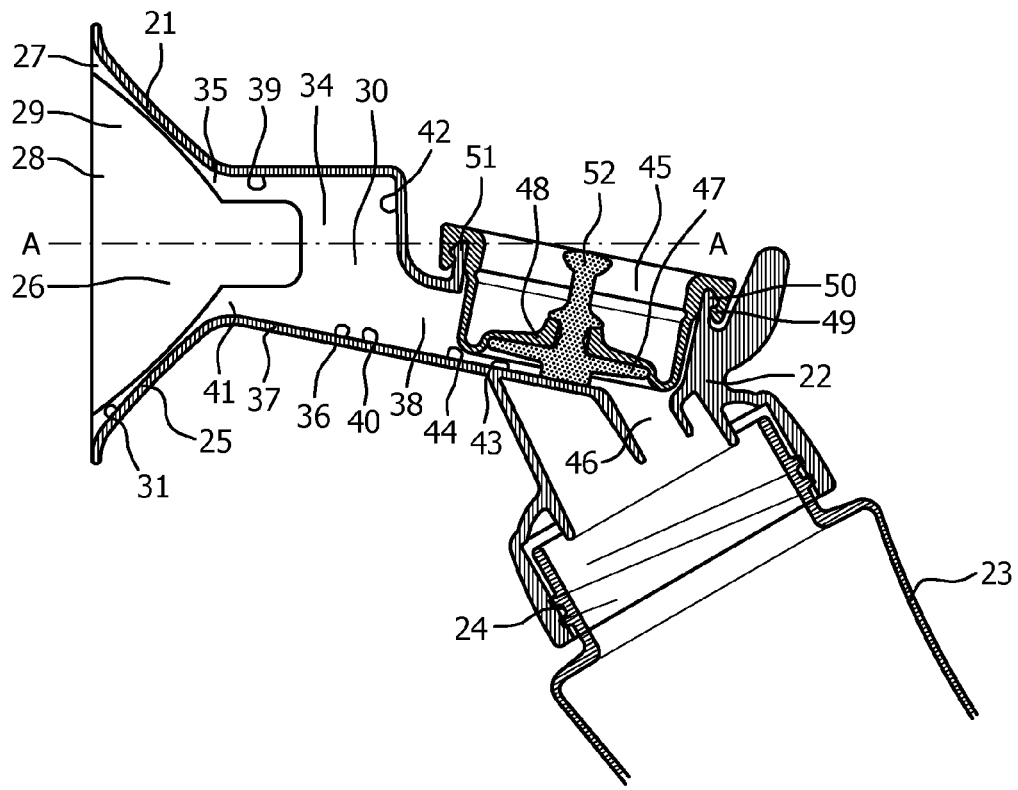
FIG. 3 shows a cross-sectional side view of a breast pump.
Figure 4:
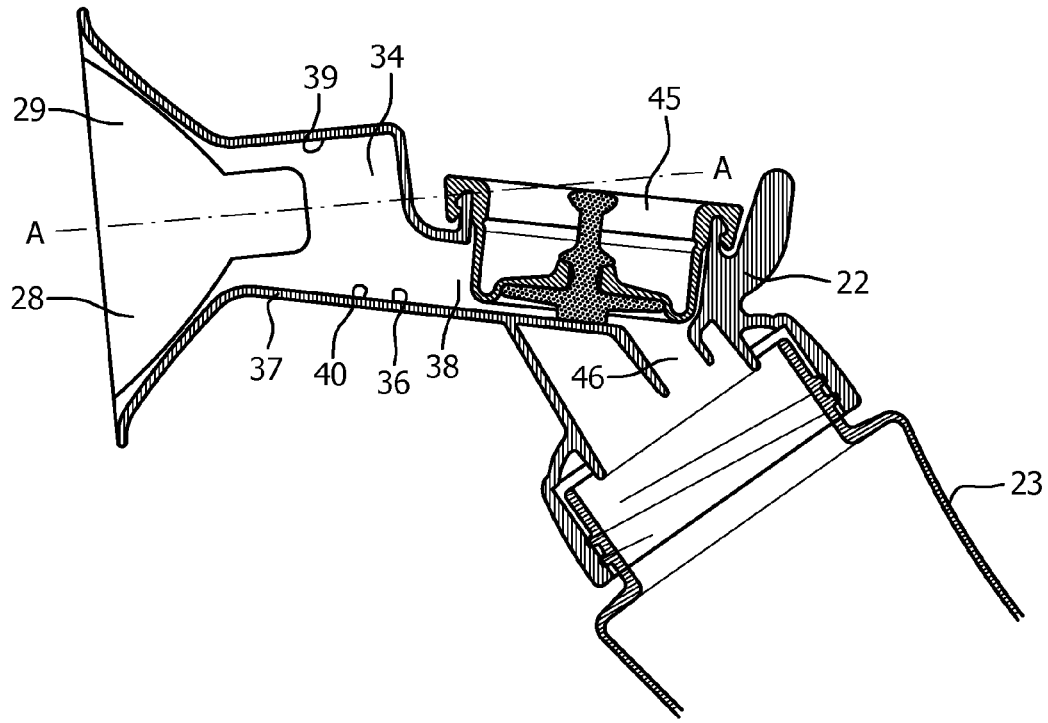
FIG. 4 shows a cross-sectional side view of the breast pump shown in FIG. 3 inclined at an angle.
Figure 5:
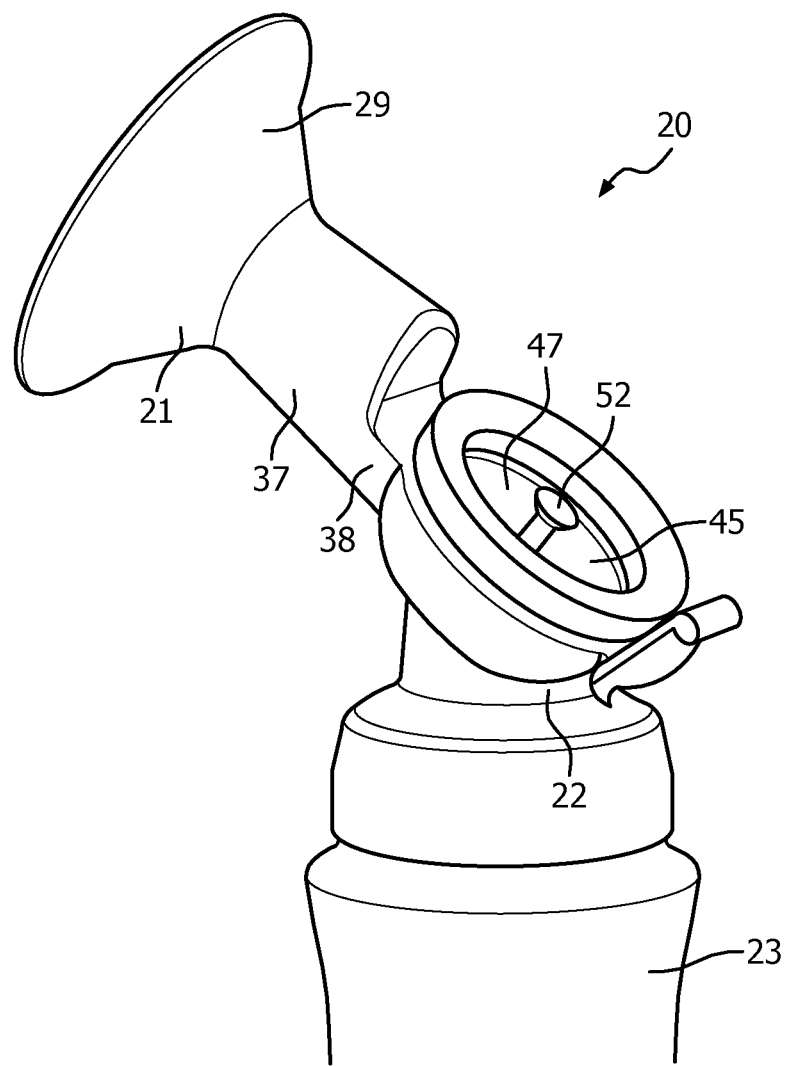
FIG. 5 shows a perspective view of the breast pump shown in FIG. 3.

Referring now to FIGS. 3 to 5, a breast pump unit 20 is shown. The breast pump comprises a breast receiving funnel 21, a main body 22 and a milk-receiving vessel 23. The milk receiving vessel 23, which may take the form of a feeding bottle for an infant or baby, is attached to the main body by a screw fitting 24, although it will be understood that alternative releasable attachment means may be used, such as clips (not shown).

The breast receiving funnel 21 extends from the main body 22 of the breast pump 20. The funnel 21 comprises an outer shell 25 and has a hollow breast receiving space 26 with an outer opening 27 for receiving the breast of a user 28. The outer shell 25 extends from the main body 22 and is integrally formed therewith.

Although in the present embodiment the funnel 21 is integrally formed with the main body 22 of the breast pump, it will be understood that in an alternative embodiment the funnel 21 is removably mounted to the main body 22. Such a funnel 21 is removably mounted to the main body 22 of the breast pump in part to aid cleaning or sterilization of the funnel 21 and main body 22, and to allow the funnel 21 to be replaced or exchanged for an alternative funnel.

The breast receiving funnel 21 comprises a circle symmetric breast receiving portion 29, defining the breast receiving space 26, and a throat portion 30. An outer end of the breast receiving portion 29 defines the outer opening 27 through which a user inserts a breast. An inner face 31 of the breast receiving portion 29 converges from the outer end towards the throat 30. The throat 30 extends between the breast receiving portion 29 and the main body 22.

The breast receiving portion 29 and throat 30 are formed by the outer shell 25 and are integrally formed with each other and the main body 22. The outer shell 25 of the funnel 21 and the main body 22 are formed from a rigid, non-deformable material, such as a rigid plastic, for ease of manufacture and to allow sterilization, although alternative suitable materials may be used. The outer shell 25 of the funnel 21 comprises an outer wall 37 with an inner surface 36 which defines a nipple receiving chamber 34 in the throat 30, as will become apparent hereinafter. An inner end 35 of the breast receiving portion 29 defines an inner opening 41 between the breast receiving portion 29 and the nipple receiving chamber 34. The nipple receiving chamber 34 is elongate and extends from an inner end 35 of the breast receiving portion 29.

The breast receiving portion 29 is conical and has a longitudinal axis A-A (FIG. 3) which extends through the centre of the outer opening 27 and the centre of the inner end 35 of the breast receiving portion 29. The throat 30 further comprises a fluid passageway 38 which extends from the nipple receiving chamber 34. The outer wall 37 extends around the nipple receiving chamber 34, and the inner surface 36 of the outer wall 37 comprises an upper section 39 and a lower section 40. The upper and lower sections 39, 40 of the inner surface 36 are formed on opposing sides of the nipple receiving chamber 34 and are integrally formed with each other, with opposing parallel side faces of the inner surface 36 extending therebetween. When the breast pump and funnel are held in a normal operable orientation, with the pump held against the breast and the milk receiving vessel 23 extending downwardly, the upper section 39 is disposed above the lower section 40.

The upper section 39 of the outer wall inner surface 36 extends parallel to the longitudinal axis A-A defined by the breast receiving portion 29. The lower section 40 of the inner surface 36 extends from the end of the nipple receiving chamber 34 proximate to the breast receiving portion 29 and is angled away from the longitudinal axis A-A defined by the breast receiving portion 29. Therefore, as the inner surface 36 of the outer wall 37 defining the nipple receiving chamber 34 extends away from the breast receiving portion 29 of the funnel 21, the lower section 40 of the of the inner surface 36 diverges away from the longitudinal axis A-A, as well as the upper section 39. In the present embodiment the lower section 40 of the inner surface 36 extends at a constant gradient away from the longitudinal axis A-A, although it will be understood that the lower section 40 of the inner surface 36 may be curved or have an alternative cross-sectional arrangement.

Although in the present embodiment the upper section 39 of the inner surface 37 extends parallel to the longitudinal axis of the breast receiving portion 29 of the funnel, it will be appreciated that the upper section 39 may also diverge away the longitudinal axis of the breast receiving portion 29 of the funnel 21. Similarly, in the present embodiment the opposing parallel side faces of the inner surface 36 extend parallel to the longitudinal axis A-A of the breast receiving portion 29, although it is envisaged that the side faces may also diverge away from each other and the longitudinal axis A-A away from the breast receiving portion of the funnel. An advantage of the upper section 39 of the inner surface 36 extending parallel to, or diverging away from, the longitudinal axis A-A is that it prevents a user's nipple in the nipple receiving chamber 34 from abutting against or contacting the inner surface 37, which may cause abrasion or rubbing of the user's nipple and cause discomfort and/or soreness.

The outer wall 37 further comprises an end surface 42 at an opposing end of the nipple receiving chamber 34 to the inner opening 41 defined between the breast receiving portion 29 and the nipple receiving chamber 34. The end surface 42 extends from the upper section 39 of the inner surface 36.

The fluid passageway 37 extends from the opposing end of the nipple receiving chamber 34 to the inner opening 41, and extends through the end surface 42. The fluid passageway 37 extends from the nipple receiving chamber 34, and extends into the main body 22 of the breast pump 20. Alternatively, the fluid passageway 37 is formed in the throat 30 of the funnel 21 only and extends to the main body 22.

The fluid passageway 38 is tubular and is defined by a side wall 43. The fluid passageway 38 extends from the lower section 40 of the outer wall inner surface 36 such that a bottom section 44 of the fluid passageway side wall 43 extends from the lower section 40 of the inner surface 36 defining the nipple receiving chamber 34. Therefore, the bottom section 44 of the fluid passageway 37 extends at a constant gradient with the lower section 38 of the inner surface 36 and forms a linear surface therewith. It will be understood that the bottom section 44 of the fluid passageway diverges away from the longitudinal axis A-A. Although in the present embodiment the bottom section 44 of the fluid passageway side wall 43 extends at a constant gradient away from the longitudinal axis A-A, it will be understood that the bottom section 44 may be curved or have an alternative cross-sectional arrangement. It will be appreciated that an end of the bottom section 44 of the fluid passageway 37 proximate the lower section 38 of the inner surface 36 defining the nipple receiving chamber 34 is not disposed above the lower section 38 to prevent pooling at that juncture. Furthermore, it is envisaged that the bottom section 44 of the fluid passageway side wall 43 may be stepped down from the lower section 38 of the inner surface 36.

A vacuum pump unit chamber 45 is formed in part of the fluid passageway 38 extending in the main body 22 of the breast pump 20. A fluid outlet 46 is formed at an opposing end of the fluid passageway 38 to the nipple receiving chamber 34. The fluid outlet 46 extends from the bottom section 44 of the fluid passageway 37 and communicates the fluid passageway 37 with the milk receiving vessel 23. Therefore, milk flowing from the nipple receiving chamber 34, along the fluid passageway 38 flows into and through the fluid outlet 46 to the milk receiving vessel 23. A fluid path along which milk expressed from a user's breast flows is therefore defined from the nipple receiving chamber 34, along the fluid passageway 38 to the fluid outlet 46, and through the fluid outlet 46 to the milk receiving vessel 23.

The fluid outlet 46 is formed at an opposing end of the fluid passageway 38 to the nipple receiving chamber 34 so that a vacuum pump unit 47 disposed in the vacuum pump unit chamber 45 is disposed between the nipple receiving chamber 34 and the fluid outlet 46. The vacuum pump unit 45 creates a negative pressure in the nipple receiving chamber 34 when a user's breast is disposed in the breast receiving space 25, as will be explained below. An advantage of forming the vacuum pump unit chamber 45 in the fluid passageway 38 is that it disposes the vacuum pump unit 47 in line with the nipple receiving chamber 34 and the fluid outlet 46, and reduces the size of the breast pump itself. Furthermore, the volume of space in which a vacuum is created is reduced, therefore increasing the efficiency of the vacuum pump unit.

The vacuum pump unit 47 extends from the main body 22, and is used to cyclically create a vacuum in the nipple receiving chamber 34, when operated. The vacuum pump unit 47 comprises a resilient, deformable diaphragm 48 disposed in the vacuum pump unit chamber 45.

The vacuum pump unit chamber 45 is spaced from the nipple receiving chamber 34 by the fluid passageway 38. This ensures that components of the vacuum pump unit 47, including the diaphragm 48, do not rub against the user's nipple when it is disposed in the nipple receiving chamber 34, and so reduces a user's discomfort.

The vacuum pump unit chamber 45 is cup shaped and the diaphragm 48 is deformable in the vacuum pump unit chamber 45 to act as a piston means. The diaphragm 48 is formed from an elastomeric material. A rim 49 of the diaphragm 48 is turned back on itself to receive an upper end 50 of a vacuum pump unit chamber wall 51 to secure the diaphragm 48 in the vacuum pump unit chamber 45. An actuating element 52 extends from the centre of the diaphragm 48. The actuating element 52 comprises a stem and a bulbous end, distal to the diaphragm 48, which is attachable to a drive means (not shown), such as a handle (not shown) mounted to the breast pump main body 22, an external pump unit or a motor (not shown).

The drive means is manually operable to deform the diaphragm 48 and cyclically cause a vacuum in the vacuum pump unit chamber 45, and therefore the nipple receiving chamber 34, as will be explained hereinafter. Alternatively, a motor is actuated to cyclically deform the diaphragm 34 and therefore create a vacuum. The motor is disposed in a motor unit (not shown) mounted to the main body 22. If an external pump unit (not shown) is employed, a tube communicates the electrically driven external pump unit with an upper side of the vacuum pump unit chamber 45 and a cyclical vacuum is generated by the external pump unit to deform the diaphragm 48. Although it is envisaged that a diaphragm is used, in an alternative embodiment a vacuum may be formed in the nipple receiving chamber 34 without use of a diaphragm.

In the present embodiment shown in FIGS. 3 to 5, the circumferentially extending vacuum pump unit chamber wall 51 perpendicularly upstands to the bottom section 44 of the fluid passageway side wall 43, however it will be appreciated that the circumferentially extending vacuum pump unit chamber wall 51 may extend at an alternative angle to the bottom section 44 of the fluid passageway side wall 43.

A valve (not shown) is disposed at an end of the fluid outlet 46. The valve is a one way valve which seals the fluid passageway 38, and therefore the nipple receiving chamber 34, from the atmospheric pressure in the milk receiving vessel (not shown) when the vacuum pump unit 47 is operable to create a vacuum in the nipple receiving chamber 34, but allows milk to flow to the milk receiving vessel.

An insert (not shown) is disposable in the breast receiving portion 29 of the funnel 21. The insert (not shown) has a circle symmetric flexible, deformable wall extending around an inner portion of the breast receiving portion 29 of the funnel 21. An inner face of the flexible, deformable wall forms the inner surface of the funnel 21 against which a user's breast locates when the insert is disposed therein. An advantage of the insert (not shown) is that it acts as a cushion to comfort a user's breast when it is disposed therein, and may be deformable against a user's breast during use to apply a compressive force to the breast to aid the expression of milk from the breast.

Operation of the breast pump funnel and breast pump according to the above exemplary embodiment will now be described with reference to FIGS. 3 to 5.

To operate the breast pump 20, a user holds the breast pump 20 by the main body 22 and inserts a breast into the breast receiving space 26 formed by the funnel 21. The user's breast then extends into the funnel 21 and the inner surface of the breast receiving portion 29 of the funnel 23 locates against the user's breast 28 to form a seal.

As the user's breast is inserted into the funnel 21, the user's nipple is inserted into the nipple receiving chamber 34 in the direction of the longitudinal axis A-A. The end of the user's nipple is then disposed in the nipple receiving chamber 34.

The user then operates the breast pump 20. The user depresses and releases the handle (not shown) to cyclically actuate the vacuum pump unit 47 such that the actuating element 52 moves in a reciprocal manner the diaphragm, the diaphragm 48 repeatedly deforms to effect a cyclical vacuum in the diaphragm chamber 45. Alternatively, when the vacuum pump unit 47 is electrically driven, the user depresses a lever to activate the motor or external pump unit. The motor or external pump unit then drives the vacuum pump unit 47 in a reciprocal manner.

As the vacuum pump unit 47 cyclically creates a vacuum in the diaphragm chamber 45, a negative pressure is created in the fluid passageway 38, and therefore the nipple receiving chamber 34 fluidly communicating with the fluid passageway 38. Similarly, a reduced pressure is effected in the breast receiving space 25 defined by the funnel 23, which is sealed by a user's breast. The fluid passageway 38 is sealed by the valve (not shown) in the fluid outlet from the atmospheric pressure in the milk receiving vessel 23.

The cyclical vacuum in the nipple receiving chamber 34 causes milk to be expressed from the end of the user's nipple, which flows into the nipple receiving chamber 34. As the user holds the breast pump in an orientation with the milk receiving vessel 23 held below the main body 22 of the breast pump, with the lower section 40 of the outer wall inner surface 36 positioned below the upper section 39 of the outer wall inner surface 36, the expressed milk falls onto the lower section 40 of the inner surface 36. Similarly, any expressed milk which is expressed against the end surface 42 of the nipple receiving chamber 34 is urged to flow onto the lower section 40.

The expressed milk falling onto the lower section 40 of the inner surface 36 then flows along the lower section 40 into the fluid passageway 38, and flows along the fluid passageway 38 to the fluid outlet 46 and into the milk receiving vessel 23. As the lower section 40 of the inner surface 36 diverges from the longitudinal axis A-A of the breast receiving portion 29 of the funnel 21, the lower section 40 of the inner surface 36 diverges away from the user's nipple, and the expressed milk flows downwardly towards the fluid outlet 46, away from the user's breast.

The expressed milk flows easily from the nipple receiving chamber 34 into the fluid passageway 38 due to the bottom section 44 of the fluid passageway side wall 43 extending linearly from the lower section 40 of the inner surface 36 defining the nipple receiving chamber 34. As the milk expressed from the user's nipple flows directly into the fluid passageway 38, the milk does not flow into the breast receiving portion 29 of the funnel 21 and so does not pool against the user's breast.

In FIG. 3, the user's breast and the breast pump 20 are shown in use in a conventional position, in which the user is sat upright to position their breast in the breast pump. In this position, milk expressed from the user's breast flows easily into the fluid passageway 38 and then into the fluid outlet 46, without pooling anywhere else in the breast pump due to the downwardly extending incline of the lower section 40 of the inner surface 36, diverging away from the longitudinal axis A-A.

Figure 1:
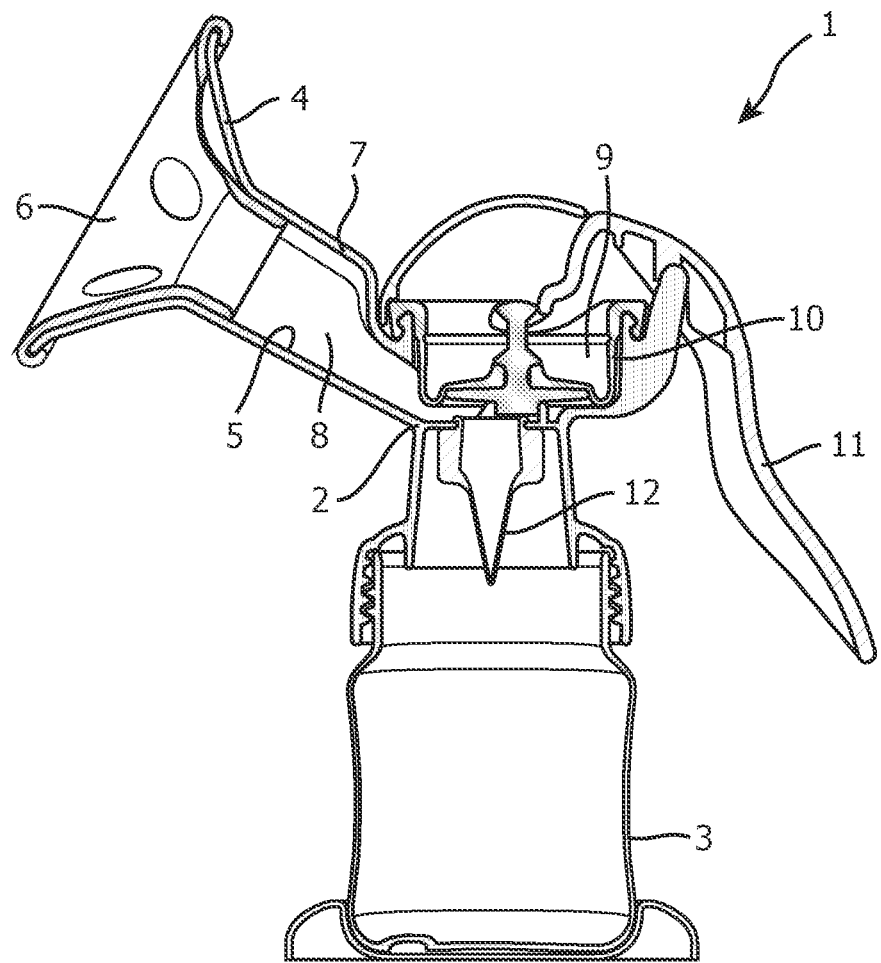
FIG. 1 shows a cross-sectional side view of an existing breast pump.
Figure 2:
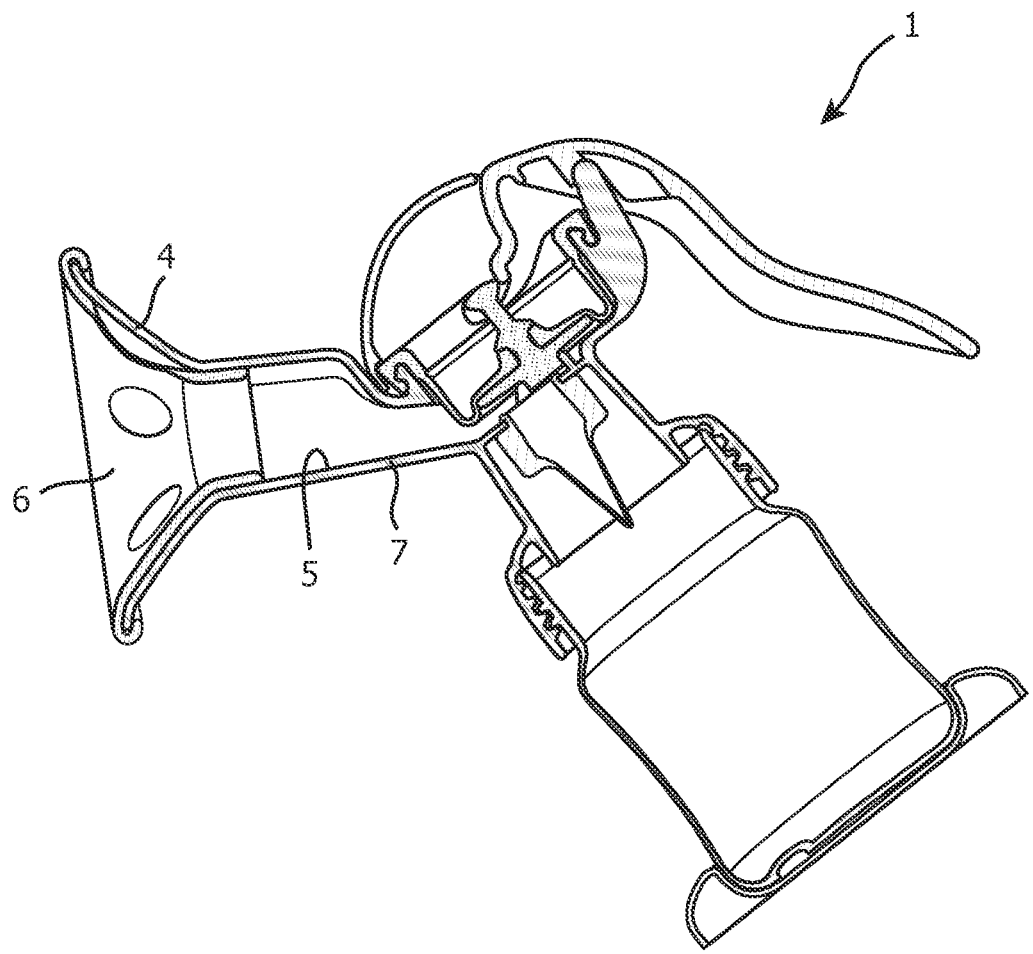
FIG. 2 shows a cross-sectional side view of the existing breast pump shown in FIG. 1 inclined at an angle.

In FIG. 4, the user's breast and breast pump are shown in use in a position in which the user leans backwards. In this position, the funnel 21 and main body 22 of the breast pump 20 are angled back towards the user. Expressed milk in a conventional breast pump used in this position would flow into the breast receiving portion of the funnel towards the user's breast (as shown in FIG. 2). However, with the present arrangement milk expressed from the user's breast flows along the lower section 40 of the outer wall inner surface 36 defining the milk receiving chamber 34, away from the user's breast and into the fluid passageway 38 because the lower section 40 of the inner surface 38 maintains a downwardly acting gradient away from the user's nipple. Therefore, expressed milk flows into the fluid passageway 38 having the same downwardly acting gradient and through the fluid outlet 46 into the milk receiving vessel 23. The expressed milk cannot flow into the breast receiving portion 29 of the funnel 21 as all the milk expressed into the nipple receiving chamber 34 flows into the fluid passageway 38.

An advantage of the user being able to lean back and still enable expressed milk to flow to the milk receiving vessel without pooling elsewhere in the breast pump, is that it enables the user to maintain a more relaxed and comfortable expression position, which improves the user's 'let down' reflex, and reduces the user's time to milk ejection reflex. In addition, the user is able to use the breast pump for a longer duration as they are in a relaxed and comfortable expression position.

When a user removes the breast pump from their breast, there is little or no milk present in the funnel. Therefore, there is no milk loss as all the milk has flowed to the milk collecting vessel, and milk does not cause discomfort from wetting the user's skin and clothing.

Furthermore, as the milk flows directly into the fluid passageway 38, it does not adhere to the inner surface of the funnel, and so less milk is wasted that does not flow to the milk collection vessel. Therefore, loss of milk expressed from a user's breast will be minimized.

In addition, as the user leans back, the breast pump and milk receiving vessel attached thereto recline with the user. Therefore, the milk receiving vessel does not abut against the user's midriff and limit the user's reclining position.

A further advantage of the present arrangement is that the nipple receiving chamber is integrally formed in the funnel of the breast pump, and so the funnel itself is configured to prevent expressed milk from pooling against a user's breast, without any additional components, for example an insert. Therefore, further features of a breast pump from which the funnel extends may be positioned relative to the funnel in an ergonomic manner to minimize physical effort and discomfort. For example, a handle extending from the breast pump will be maintained in a desired operating position with respect to the user irrespective of the user's position.

In the present embodiment, the outer wall 36 defining the nipple receiving chamber 34 is formed from a transparent plastic. Therefore, it is possible for the user to view the nipple in the nipple receiving chamber 34 during milk expression.

Additionally, the vacuum pump unit chamber 45 is disposed in the fluid passageway, and so the volume of space in which the vacuum pump unit has to create a vacuum is reduced, which makes the vacuum pumping action more efficient and allows a lower pressure to be generated in the nipple receiving chamber 34.

Although claims have been formulated in this application to particular combinations of features, it should be understood that the scope of the disclosure of the present invention also includes any novel features or any novel combinations of features disclosed herein either explicitly or implicitly or any generalization thereof, whether or not it relates to the same invention as presently claims in any claim and whether or not it mitigates any or all of the same technical problems as does the parent invention. The applicants hereby give notice that new claims may be formulated to such features and/or combinations of features during the prosecution of the present application or of any further application derived therefrom.

The invention claimed is:

1. A breast pump comprising a funnel having a breast receiving portion and a nipple receiving chamber to receive a user's nipple, a fluid passageway extending from the nipple receiving chamber along which milk expressed from a user's nipple is able to flow, and a vacuum pump unit chamber for receiving a vacuum pump unit to generate a vacuum in the nipple receiving chamber, the nipple receiving chamber being defined by an inner surface of an outer wall, wherein the inner surface of the outer wall of the nipple receiving chamber extends from the breast receiving portion, and a lower section of the inner surface of the nipple receiving chamber diverges away from an opposing upper section of the inner surface, wherein the vacuum pump unit chamber is formed in the fluid passageway, and wherein the vacuum pump unit has a longitudinal axis that is parallel to the longitudinal axis of the fluid receiving chamber.

2. A breast pump according to claim 1, wherein the breast receiving portion has a longitudinal axis and the lower section of the inner surface diverges away from the longitudinal axis of the breast receiving portion.

3. A breast pump according to claim 2, wherein the upper section of the inner surface extends parallel to the longitudinal axis of the breast receiving portion.

4. A breast pump according to claim 2, wherein the outer wall further comprises an end surface extending from the upper section of the inner surface.

5. A breast pump according to claim 1, wherein the fluid passageway extends from the lower section of the inner surface.

6. A breast pump according to claim 5, wherein the fluid passageway extends parallel to the lower section of the inner surface.

7. A breast pump according to claim 5, wherein the fluid passageway is formed in the end surface of the nipple receiving chamber.

8. A breast pump according to claim 1, further comprising a fluid outlet extending from the fluid passageway which communicates between the fluid passageway and a milk collection vessel for receiving milk expressed from a user's nipple, wherein the fluid outlet extends downwardly from the fluid passageway so that milk falls towards a milk collection vessel.

9. A breast pump according to claim 8, wherein a bottom section of a side wall of the fluid passageway extends from the lower section of the inner surface to the fluid outlet.

10. A breast pump according to claim 9, wherein a valve is disposed at a lower end of the fluid outlet spaced from the bottom section of the side wall of the fluid passageway.

11. A breast pump according to claim 8, wherein the vacuum pump unit chamber is disposed between the nipple receiving chamber and the fluid outlet.

12. A breast pump according to claim 1, wherein the vacuum pump unit comprises a deformable diaphragm including an actuating element extending therefrom to deform the diaphragm when the vacuum pump is actuated.

13. A breast pump according to claim 12, wherein the deformable diaphragm is disposed in the vacuum pump unit chamber formed in the fluid passageway.

14. A breast pump according to claim 13, wherein a the deformable diaphragm is disposed in the vacuum pump unit chamber formed in the fluid passageway.

* * * * *